United States Patent
Clarke et al.

(10) Patent No.: US 9,581,576 B2
(45) Date of Patent: Feb. 28, 2017

(54) DUAL SENSOR ANALYZER

(71) Applicant: Envent Engineering Ltd., Calgary (CA)

(72) Inventors: Randy Clarke, Calgary (CA); David Kirk, Calgary (CA); Larry Siebold, Calgary (CA); Ryan Jahn, Calgary (CA)

(*) Notice: Subject to any disclaimer, the term of this patent is extended or adjusted under 35 U.S.C. 154(b) by 53 days.

(21) Appl. No.: 14/502,686

(22) Filed: Sep. 30, 2014

(65) Prior Publication Data

US 2016/0091477 A1    Mar. 31, 2016

(51) Int. Cl.
| | |
|---|---|
| *G01N 21/00* | (2006.01) |
| *G01N 31/00* | (2006.01) |
| *G01N 33/00* | (2006.01) |
| *C12Q 1/68* | (2006.01) |
| *G01N 35/00* | (2006.01) |
| *G01N 31/22* | (2006.01) |

(52) U.S. Cl.
CPC ....... *G01N 33/0044* (2013.01); *G01N 31/224* (2013.01)

(58) Field of Classification Search
CPC .......... C12Q 1/68; G01N 35/00; G01N 21/00; G01N 31/00; G01N 33/00
USPC ........ 422/50, 83, 82.05, 63, 66; 436/43, 164
See application file for complete search history.

(56) References Cited

U.S. PATENT DOCUMENTS

| | | | | |
|---|---|---|---|---|
| 4,127,780 | A * | 11/1978 | Kimbell | 250/559.01 |
| 5,206,519 | A * | 4/1993 | Kirk | 250/565 |
| 2009/0246883 | A1* | 10/2009 | McBrady et al. | 436/164 |

* cited by examiner

*Primary Examiner* — Brian J Sines
(74) *Attorney, Agent, or Firm* — Brion Raffoul

(57) ABSTRACT

Systems, methods, and devices for testing gaseous samples for concentrations of specific chemicals. An apparatus has two sensing assemblies for testing for hydrogen sulfide concentrations in gaseous samples. A first assembly is disposed to expose a first side of a sensing tape to a first stream of a gaseous sample. A second assembly is disposed to expose a second side of the same sensing tape to a second stream of another gaseous sample. Both assemblies detect and analyze the hydrogen sulfide concentrations of their respective gaseous samples by way of their respective sides of the sensing tape.

9 Claims, 5 Drawing Sheets

DUAL SENSOR ANALYZER

TECHNICAL FIELD

The present invention relates to testing equipment. More specifically, the present invention relates to equipment for testing for concentrations of specific substances.

BACKGROUND OF THE INVENTION

The presence of hydrogen sulfide in natural gas, liquid petroleum gas (LPG), and even in crude petroleum has led to a need to determine hydrogen sulfide concentrations in different samples. $H_2S$ detection that is fast and reliable is the cornerstone of many industrialized processes that cannot tolerate $H_2S$ in their gas due to fatal consequences for humans and degradation of physical assets such as pipelines.

To determine hydrogen sulfide concentrations, the chemical reaction

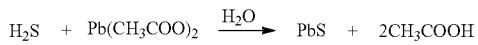

is used. This reaction is implemented by using paper tape impregnated or covered with lead acetate. The paper tape is immersed in a liquid bath with lead acetate, thereby leaving the paper capable of detecting $H_2S$. Instead of hydrogen sulfide concentration, the same reaction can be used to determine total sulfur concentration by mixing the sample gas with hydrogen then heating the resulting gas to approximately 900 C where all sulphurs are changed into $H_2S$.

The above processes are well-known and are detailed in U.S. Pat. Nos. 4,127,780 and 5,206,519. The contents of these documents are hereby incorporated in its entirety by reference.

The issue with current testing equipment is that, currently, only one side of the testing tape is used. This leads to waste and inefficiencies as each sensing tape is only used once and is then discarded. As well, due to the cost of a single analyzer of the above type, most users that require analysis on more than one stream of gas will utilize a stream switching technique on a single analyzer rather than purchasing multiple analyzers. Stream switching implies that the stream(s) currently not being analyzed can encounter a rise in the $H_2S$ concentration to unacceptable levels and this rise in $H_2S$ concentration may be undetected.

SUMMARY OF INVENTION

The present invention provides systems, methods, and devices for testing gaseous samples for concentrations of specific chemicals. An apparatus has two sensing assemblies for testing for hydrogen sulfide concentrations in gaseous samples. A first assembly is disposed to expose a first side of a sensing tape to a first stream of a gaseous sample. A second assembly is disposed to expose a second side of the same sensing tape to a second stream of another gaseous sample. Both assemblies detect and analyze the hydrogen sulfide concentrations of their respective gaseous samples by way of their respective sides of the sensing tape.

In a first aspect, the present invention provides a system for analyzing gaseous samples, the system comprising:
- a sensing tape having a first side and a second side, said first side being exposed to a first stream of a first gaseous sample and said second side being exposed to a second stream of a second gaseous sample;
- a first sensing assembly for sensing a concentration of a first substance from said first stream from said first side of said sensing tape, said first sensing assembly including a first sensor;
- a second sensing assembly for sensing a concentration of a second substance from said second stream from said second side of said sensing tape, said second sensing assembly including a second sensor;

wherein
said first side of said sensing tape passes by said first sensor such that said first sensor senses a quality of said first side after said first side has been exposed to said first stream;
said second side of said sensing tape passes by said second sensor such that said second sensor senses a quality of said second side after said second side has been exposed to said second stream.

In a second aspect, the present invention provides a system for analyzing samples, the system comprising:
- a sensing tape having a first side and a second side, said first side being exposed to a sample of a first substance and said second side being exposed to a sample of a second substance;
- a first sensing assembly for analyzing a first specific chemical of said first stream from said first side of said sensing tape, said first sensing assembly including a first sensor;
- a second sensing assembly for analyzing a second specific chemical of said second stream from said second side of said sensing tape, said second sensing assembly including a second sensor;

wherein
said first side of said sensing tape passes by said first sensor such that said first sensor senses a quality of said first side after said first side has been exposed to said first sample of said first substance;
said second side of said sensing tape passes by said second sensor such that said second sensor senses a quality of said second side after said second side has been exposed to said second sample of said second substance.

BRIEF DESCRIPTION OF THE DRAWINGS

The embodiments of the present invention will now be described by reference to the following figures, in which identical reference numerals in different figures indicate identical elements and in which.

DETAILED DESCRIPTION

Figure 1:
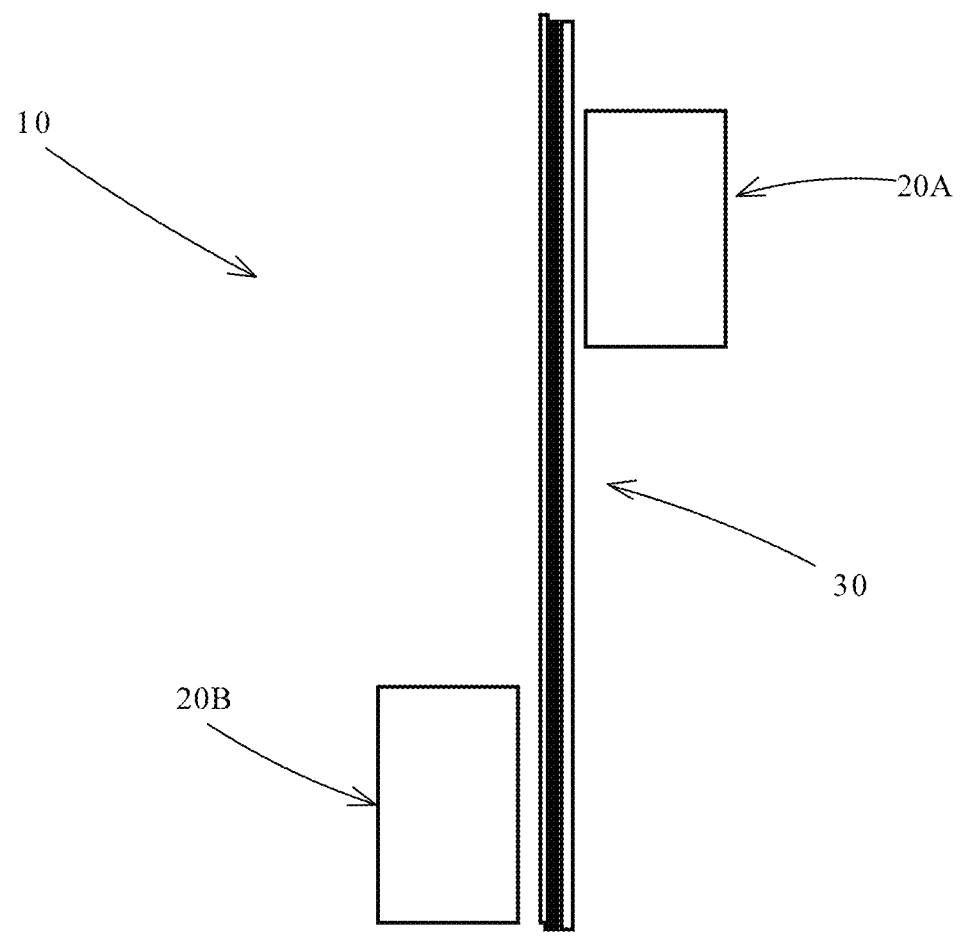
FIG. 1 is a block diagram of a system according to one aspect of the invention.

Referring to FIG. 1, a block diagram of one aspect of the invention is illustrated. As can be seen, the system 10 has two sensing assemblies 20A, 20B, each of which is adjacent a sensing tape 30. Each of the two sides of the sensing tape 30 is exposed, independently, to a separate stream of a gaseous sample. Each sensing assembly 20A, 20B is able to sense and detect the hydrogen sulfide concentration of its respective gaseous sample from its respective side of the sensing tape 30. Thus, a first side of the sensing tape is exposed to a first stream of a first gaseous sample and this first side is analyzed and detected by a first sensing assembly 20A. Similarly, a second side of the sensing tape is exposed to a second stream of a second gaseous sample and this second side is analyzed and detected by a second sensing assembly 20B. The sensing tape 30 is illustrated has having a coating on each of its two sides.

Figure 2:
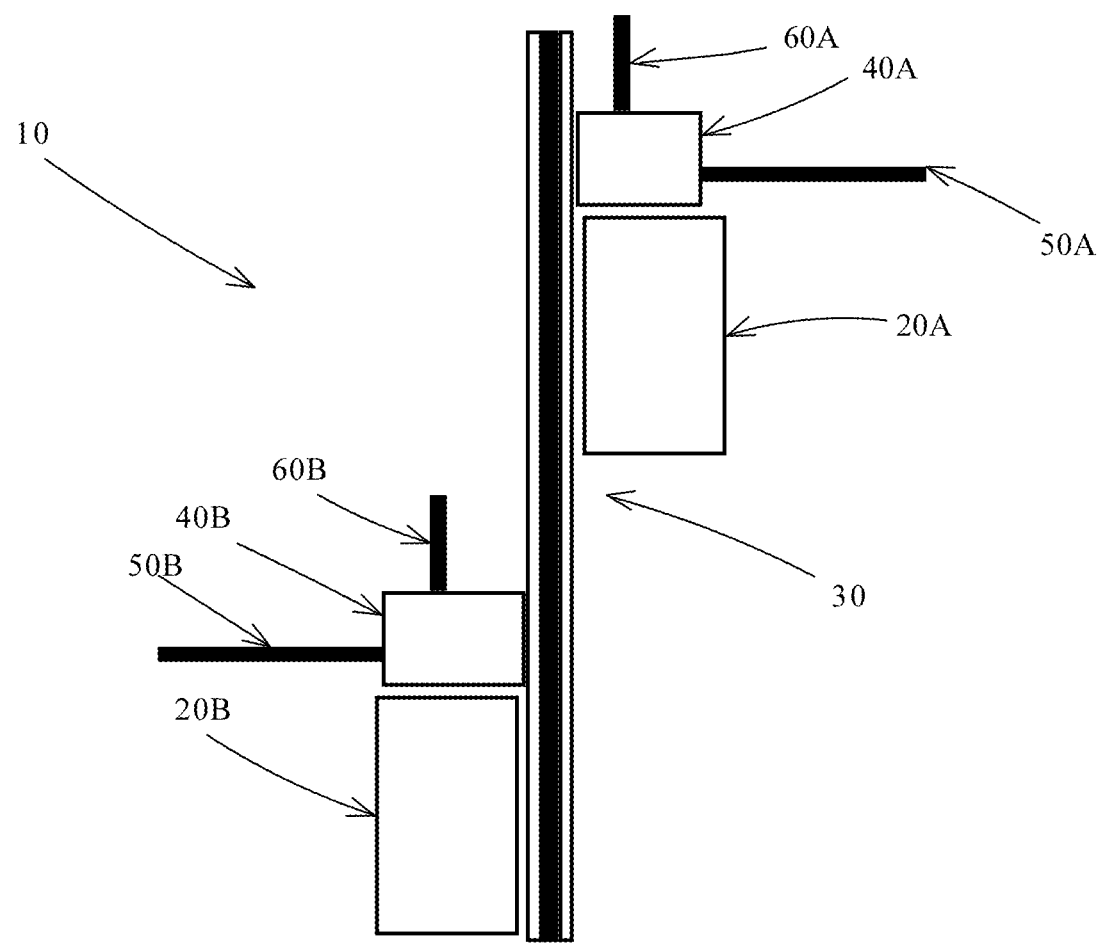
FIG. 2 is a variant of the system illustrated in FIG. 1.

The configuration of the system may depend on the implementation but a sample configuration is provided in FIG. 2. In this configuration, one side of the sensing tape passes by a first sample chamber 40A and that side of the sensing tape is exposed to a first stream of a first gaseous sample. The first sample chamber has an input pipe 50A through which the first gaseous sample enters the chamber 40A. The sample chamber also has a venting pipe 60A through which the gaseous sample exits the sample chamber 40A. The sensing tape then passes by the first sensing assembly so that the side exposed to the first gaseous sample can be analyzed by the first sensing assembly. After passing by the first sensing assembly, the sensing tape then passes by a second sample chamber 40B which exposes the other side of the sensing tape to a second stream of a second gaseous sample. The second sample chamber 40B has an input pipe 50B through which the second gaseous sample enters the chamber 40B. The second sample chamber 40B also has a venting pipe 60B through which the gaseous sample exits the sample chamber 40B. After being exposed to this second stream, the sensing tape then passes by the second sensing assembly so that the second exposed side can be analyzed by the second sensing assembly.

The various components of the system can be arranged vertically such that each sample chamber is stacked above its corresponding sensing assembly. Alternatively, the system can be arranged horizontally such that each sample chamber is adjacent or beside its corresponding sensing assembly.

Each sensing assembly can be configured to be equipped with optical means to detect staining on its side of the sensing tape with the staining being caused by a gaseous sample. In one embodiment of the invention, useful for determining hydrogen sulfide or for determining total sulfur, the sensing assembly may be configured as illustrated in FIG. 3.

Figure 3:
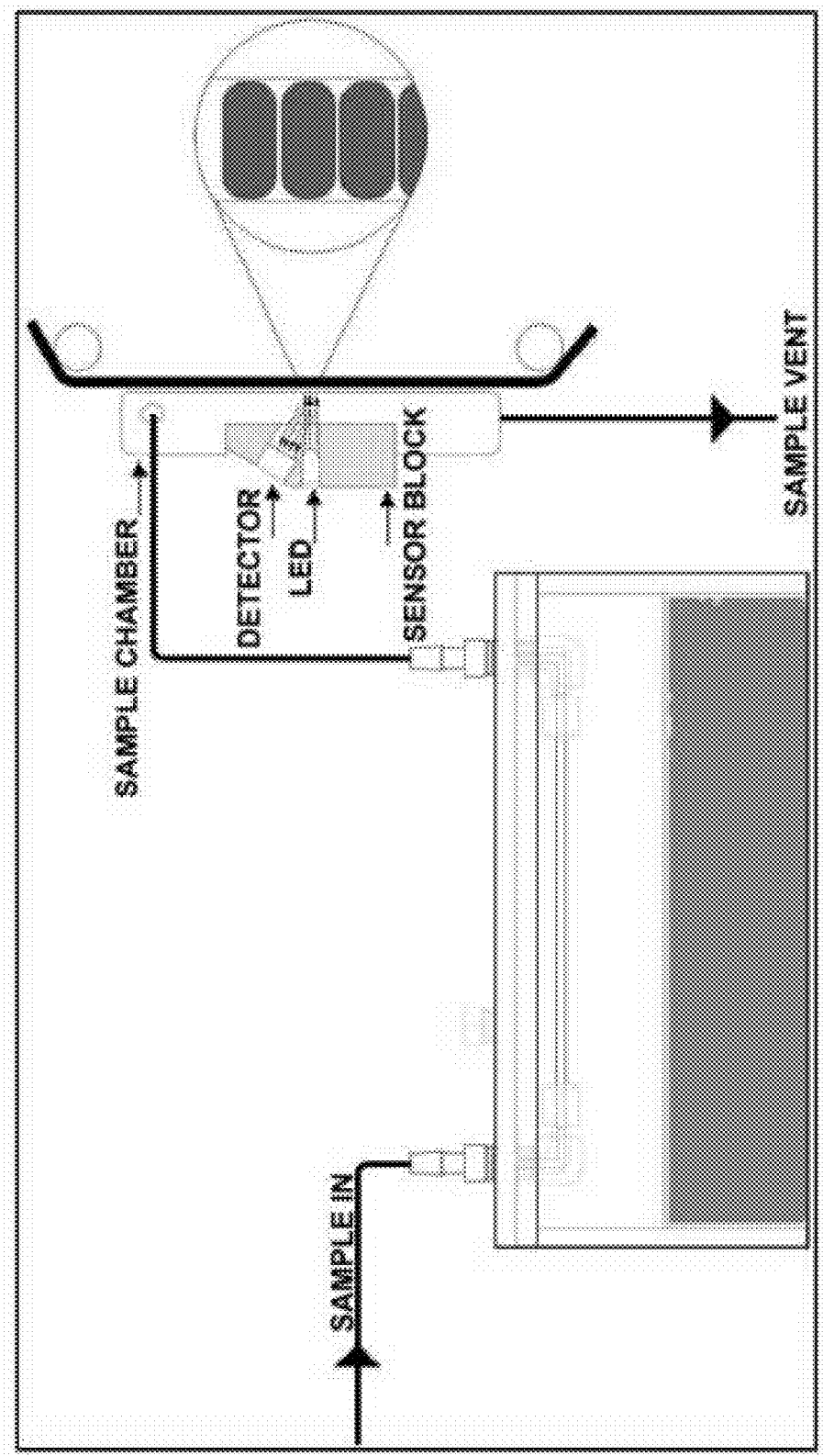
FIG. 3 is a diagram illustrating a sensing assembly according to one aspect of the invention.

Referring to FIG. 3, the sensing assembly uses a light emitting diode (LED) to illuminate a portion of one side of the sensing tape which has been exposed to the gaseous sample. For this implementation, the gaseous sample stains the portion of sensing tape it comes into contact with. The amount of staining on the exposed sensing tape is indicative of the concentration of hydrogen sulfide in the gaseous sample. The LED illuminates the exposed section and, based on how much of this illumination is reflected back, a reading of the hydrogen sulfide concentration can be derived. To detect the amount of light reflected back, the sensing assembly uses a light detector as illustrated in FIG. 3.

As can also be seen in FIG. 3, the gaseous sample enters the system and passes through a water bath or humidifier before being used to stain one side of the sensing tape. The gaseous sample is then vented out.

Figure 4:
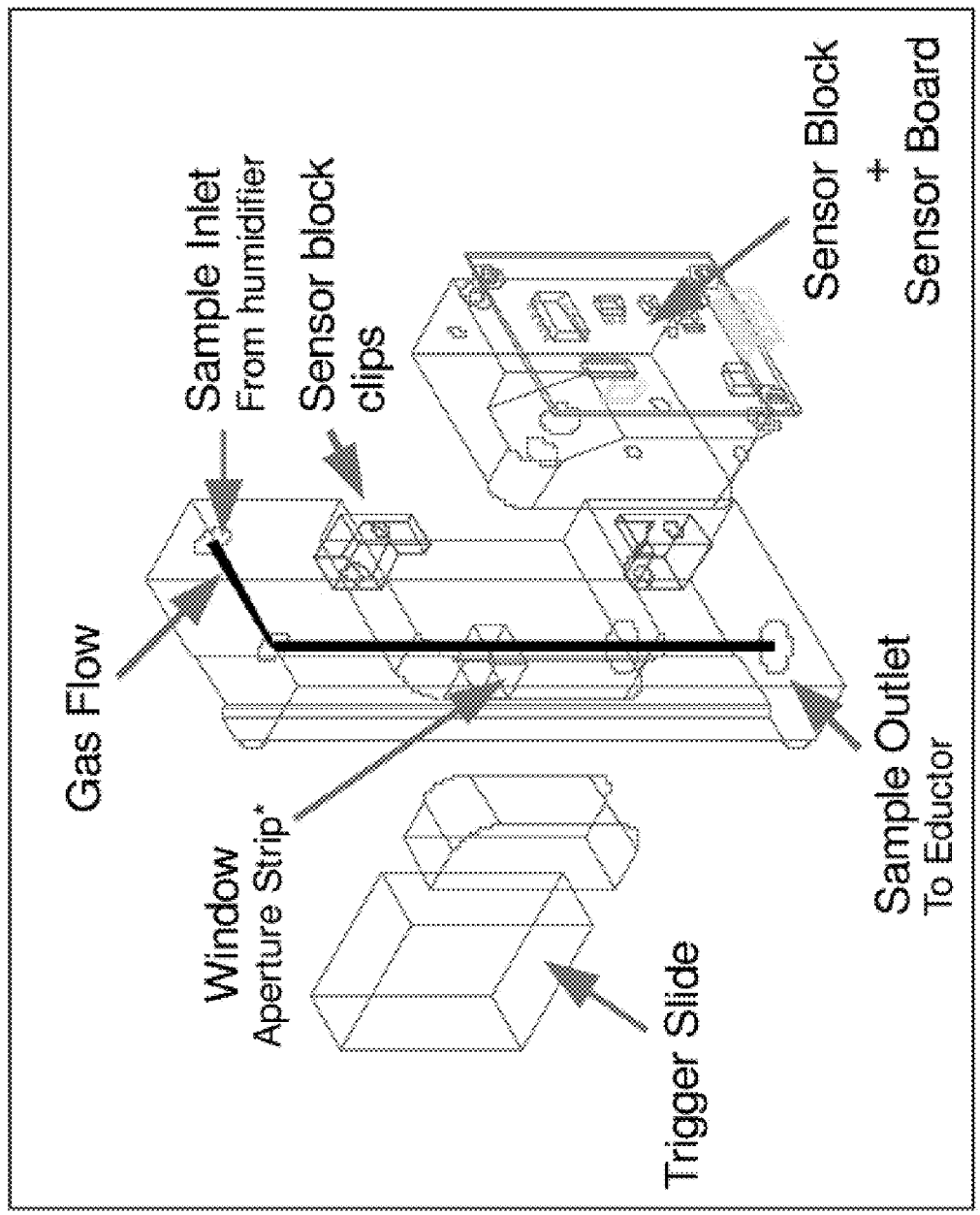
FIG. 4 is a diagram illustrating the gas flow and the components of a sensing assembly.

To better illustrate the configuration of the sensing assembly and its use of a sample chamber, FIG. 4 is provided. FIG. 4 illustrates the flow of the gaseous sample as it passes by a sample chamber equipped with a window through which the sensing tape is exposed to the sample. Once the gaseous sample has passed by the sample chamber, the sample may be vented by way of an eductor. A configuration for such an eductor is illustrated in FIG. 5.

To explain the need and/or necessity for an eductor, the reading made by a sensing assembly can be affected by positive or negative pressure on the sample vent line. This can be caused by strong winds blowing across or directly into the vent or by mechanical venting caused by external sources such as an exhaust fan. An eductor eliminates external influences on the sensing assembly reading. In cold climates, since the system is venting a moist sample, freezing can occur. The eductor will help prevent freezing problems in the vent line due to the increased velocity and drying effect of the sweep gas.

Figure 5:
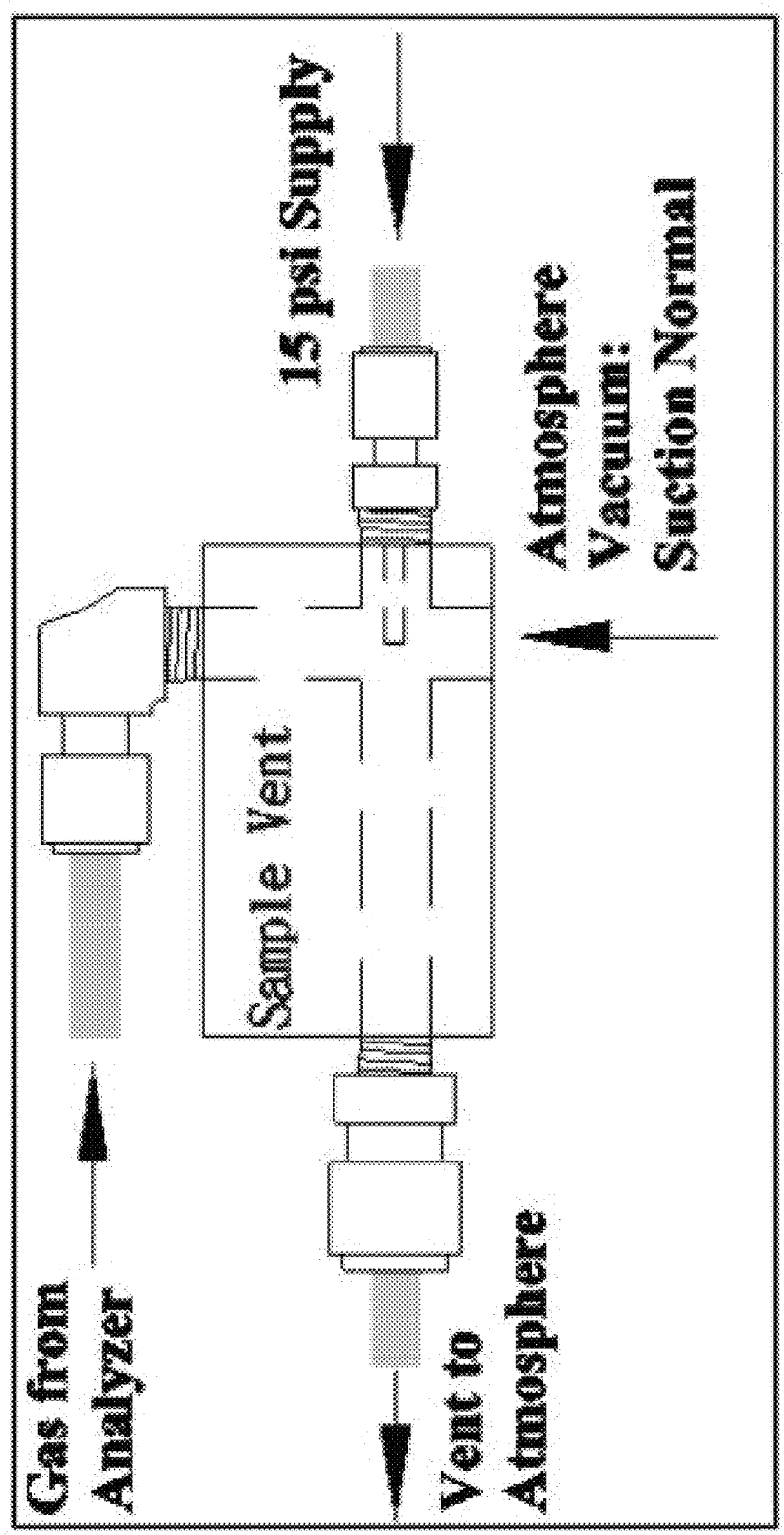
FIG. 5 is a diagram illustrating the components of an eductor.

As can be seen from FIG. 5, gas from the system is sent to a vent chamber (labeled as sample vent in the Figure). A positive pressure is provided to the sample by way of the supply from the right of the figure. A vacuum is provided by way o the connection to the bottom of the figure. It should be noted that the eductor is not necessary for the system to work. However, it has been found that the use of an eductor may help improve system performance.

In one implementation, the sensing tape is a paper tape which has been impregnated or covered with lead acetate. For this implementation, the sensors in the sensing assemblies detect variant levels of light intensity due to a color change on the sensing tape impregnated with lead acetate and which has been exposed to $H_2S$. The concentration of $H_2S$ can be determined relative to the rate at which the paper tape changes color or varies the light intensity. The sensing tape is non-permeable to the lead acetate nor to the $H_2S$. This allows for the amount of chemical reaction available for the color change to not be affected by exposing the opposite side of the paper tape to $H_2S$.

It should be noted that while the above implementation refers to $H_2S$ and/or sulfur concentrations in the gaseous samples, the system may be used to determine concentrations of other chemicals or substances. Other chemicals which react with other substances and which stains a sensing tape may be used. For these implementations, the coating on the sensing tape as well as the various substances and chemicals used would need to be adjusted and/or replaced. As well, it should be noted that while the above implementation details a gaseous sample, other non-gaseous samples may be used. Any stream (perhaps run through a mechanism which turns the liquid or solid into an aerosol) may be used. Similarly, a mechanism which allows for contact between the sensing tape and a solid, liquid, or gaseous sample may also be used.

For other implementations, the sensing tape may be made from substances other than paper. Preferably, the substrate used for the sensing tape is capable of being rolled into rolls as this method of packaging is convenient and easy to use. If packaged into rolls, as in the hydrogen sulfide implementation, the sensing tape can be easily mounted on to reels and can be easily replaced within the system. As well, passing the sensing tape by the different sample chambers and sensing assemblies would be easier as the reels would simple need to be rotated to move the sensing tape past these system components. It is also preferable that the substrate be impermeable to the coating or the substance used on the sensing tape as well as to the substances the sensing tape is exposed to. By rendering the substrate impermeable to these substances, one test and analysis can be done on one side of the sensing tape without contamination or interference from the tests being conducted on the other side. Of course, it is preferable that the substance used to coat the sensing tape is reactive in some visible manner to a component or chemical in the sample substance to which the sensing tape is exposed to. Such a visible reaction would allow for the optical sensor to be used as in the hydrogen sulfide example. Other ways by which the coating substance on the sensing tape reacts to the substances to which the sensing tape is exposed to may, of course, also be used.

It should further be noted that, when using the two sensing assemblies, these sensing assemblies need not be configured to detect and analyze for the same substance. One sensing assembly may be configured to detect $H_2S$ concentration using one sample stream while the other sensing assembly may be used to detect and analyze for another substance using the other sample stream. Conversely, the two sensing assemblies may be configured to detect and analyze for similar substances. As an example, one sensing assembly may be configured to detect and analyze for $H_2S$ concentration in one sample stream. The other sensing assembly may then be configured to detect and analyze for total sulfur concentration using another sample stream. Of course, the two sample streams may be from different sources or they may be from the same source.

A person understanding this invention may now conceive of alternative structures and embodiments or variations of the above all of which are intended to fall within the scope of the invention as defined in the claims that follow.

We claim:

1. A system for analyzing gaseous samples, the system comprising:
    a sensing tape having a first side and a second side, said first side being a front side and said second side being a reverse side, said first side being exposed to a first stream of a first gaseous sample and said second side being exposed to a second stream of a second gaseous sample;
    a first sensing assembly for sensing a concentration of a first substance from said first stream from said first side of said sensing tape, said first sensing assembly including a first sensor;
    a second sensing assembly for sensing a concentration of a second substance from said second stream from said second side of said sensing tape, said second sensing assembly including a second sensor;
wherein
    said sensing tape is mounted on at least one reel, a rotation of said at least one reel causing a first side of said sensing tape to move adjacently past said first sensor and causing said second side of said sensing tape to move adjacently past said second sensor;
    when said first side of said sensing tape is moved past said first sensor, said first sensor senses a quality of said first side after said first side has been exposed to said first stream;
    when said second side of said sensing tape is moved past said second sensor, said second sensor senses a quality of said second side after said second side has been exposed to said second stream.

2. A system according to claim 1 wherein said quality of said first side and said second side is a staining of said sensing tape, said staining being caused by exposure of said tape to said first or second gaseous sample.

3. A system according to claim 1 wherein said sensing tape is coated with lead acetate.

4. A system according to claim 1 wherein each sensing assembly comprises a separate sampling chamber, said sampling chamber being where said sensing tape is exposed to said first or second stream of gaseous sample.

5. A system according to claim 3 wherein said sensing tape is impermeable to said lead acetate.

6. A system according to claim 2 wherein at least one of said first sensor and said second sensor is an optical sensor.

7. A system according to claim 1 wherein at least one of said first and second substance is hydrogen sulfide.

8. A system according to claim 1 wherein at least one of said first and second substance is sulfur.

9. A system according to claim 6 wherein at least one of said sensing assemblies comprises lighting device for providing illumination said sensing tape, a level of reflection of said illumination being detected by said optical sensor.

* * * * *